United States Patent [19]

Tayot et al.

[11] 4,308,254

[45] Dec. 29, 1981

[54] MATERIAL ABLE TO FIX REVERSIBLY BIOLOGIAL MACROMOLECULES, ITS PREPARATION AND ITS APPLICATION

[75] Inventors: Jean-Louis Tayot, La Tour de Salvagny; Michel Tardy, Lyons, both of France

[73] Assignee: Institut Merieux, Lyons, France

[21] Appl. No.: 944,121

[22] Filed: Sep. 19, 1978

[30] Foreign Application Priority Data

Sep. 19, 1981 [FR] France ............................. 77 28163

[51] Int. Cl.$^3$ .................... A61K 37/04; A61K 39/00; A61K 39/12; A61K 39/106
[52] U.S. Cl. ..................................... 424/124; 424/12; 424/87; 424/88; 424/92
[58] Field of Search .................. 252/430, 428; 424/12, 424/88, 92, 124; 435/4, 57, 177, 181; 427/2; 23/230.6, 253 R; 260/112 R

[56] References Cited

U.S. PATENT DOCUMENTS

| 3,694,163 | 9/1972 | Sherelis | 23/253 TP |
| 3,959,079 | 5/1976 | Mareschi et al. | 435/181 |
| 3,959,080 | 5/1976 | Orth et al. | 435/181 |
| 3,963,441 | 6/1976 | Dietrich | 23/253 R |
| 3,983,053 | 9/1976 | Courtney et al. | 252/430 |
| 4,039,652 | 8/1977 | Adams et al. | 424/1 |
| 4,059,685 | 11/1977 | Johnson | 424/12 |
| 4,069,352 | 1/1978 | Parsons | 427/2 |
| 4,081,244 | 3/1978 | Polito et al. | 23/230.6 |
| 4,081,245 | 3/1978 | Polito | 23/230.6 |
| 4,081,329 | 3/1978 | Jaworek et al. | 435/181 |
| 4,125,492 | 11/1978 | Cuatrecasas et al. | 260/9 |
| 4,141,857 | 2/1979 | Levy | 252/430 |

OTHER PUBLICATIONS

Chemical Abstracts, vol. 86 (1977), p. 135338n.
Chemical Abstracts, vol. 82 (1975), p. 40435w.

Primary Examiner—Shep K. Rose
Attorney, Agent, or Firm—Cushman, Darby & Cushman

[57] ABSTRACT

A process for preparing a porous solid material for use in a chromatography column and which is capable of fixing reversibly biological macromolecules comprises coating a porous inorganic support with a polysaccharide polymer having α-glycol groups which undergo oxidative scission, subjecting the polysaccharide polymer to an oxidative scission reaction, reacting the resulting oxidized polysaccharide polymer with an amino molecule or macromolecule having the formula R'—NH$_2$ to produce a polysacchride polymer having the formula R$_4$—CH=N—R' and reducing the imine bond in said immediately above defined polysaccharide polymer to a stable amine bond.

21 Claims, No Drawings

MATERIAL ABLE TO FIX REVERSIBLY BIOLOGIAL MACROMOLECULES, ITS PREPARATION AND ITS APPLICATION

This invention has for its object a new material capable of fixing in a reversible manner biological macromolecules, its preparation and its application.

This invention more precisely has for its object new porous solid materials for use as stationary phases in chromatography columns, characterized by the fact they are made up of a porous inorganic support coated with a polysaccharide polymer, or by a modified polysaccharide polymer of formula I:

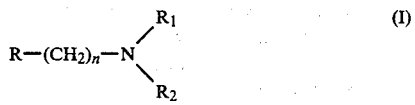

wherein R represents a polysaccharide polymer residue, n is a whole number that can vary from 1 to 10 and preferably from 2 to 5, $R_1$ and $R_2$, identical or different, represent a lower alkyl radical or hydroxyl lower alkyl radical, said polysaccharide coating, if necessary, being in the cross-linked state to promote its stability, and because on said polysaccharide or modified polysaccharide coating are grafted amino molecules or macromolecules able to constitute a reactive site in chromatography, said amino molecule or macromolecule having the formula $R'$—$NH_2$, being the residue of said amino molecule or macromolecule, the grafting bond of said amino molecule or macromolecule having the formula:

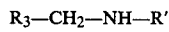

$$R_3—CH_2—NH—R'$$

$R'$ is defined as above and $R_3$—$CH_2$— represents the residue of said polysaccharide polymer or said modified polysaccharide polymer after the latter has been subjected to an oxidative scission followed by a reduction. In the above "lower alkyl" designates an alkyl radical having 1 to 4 and preferably 1 or 2 carbon atoms.

The polysaccharide and modified polysaccharide polymers that can be used to make the porous solid material of the invention are modified or unmodified polysaccharide polymers able to give rise to the well known reaction of oxidative scission with oxidizing agents such as periodates or lead tetracetate.

According to the preferred embodiments:

the porous inorganic support is made up particularly of metal oxide such as silica, alumina, magnesia or a titanium oxide, or synthetic or natural derivatives of these oxides such as glasses, silicates, borosilicates, kaolin, etc.;

the polysaccharide polymer is particularly cellulose;

the modified polysaccharide polymer is a polymer of formula I in which R is a residue of dextran, starch or cellulose and particularly diethylaminoethyldextran, DEAE dextran, diethylaminoethyl starch or diethylaminoethylcellulose;

the polysaccharide polymer coating is stabilized by cross-linking if necessary, the cross-linking agent being, for example, a dicarbonyl compound, a halohydrin or a diepoxide, particularly 1,4-butanedioldiglycidylether, epichlorohydrin, epibromohydrin, or an epoxide of the formula:

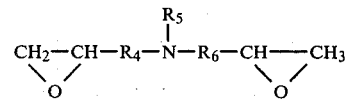

wherein $R_5$ is an alkyl having 1 to 20 carbon atoms, preferably a lower alkyl having from 1 to 4 carbon atoms and $R_4$ and $R_6$ represent a hydrocarbon chain having 1 to 10 carbon atoms, preferably a lower alkylene radical having 1 to 4 carbon atoms;

the amino molecule or macromolecule of formula $R'$—$NH_2$, able to act as a reactive site in chromatography, can be any molecule carrying $NH_2$ functions usable in chromatography with biospecific, chemical or physical-chemical affinity. It is a matter of molecules able to give rise to reversible interactions of the biospecific, chemical or physico-chemical type, for example, ionic interactions, interactions causing the intervention of hydrophobic properties, interactions causing the intervention of a biospecific or chemical affinity, for example, the formation of reversible complexes. The amino molecule or macromolecule can have a cationic character able to be advantageously used in anion exchange reactions; it can comprise anionic groups such as carboxyl or sulfonic groups, and give rise to cation exchange reactions; it can also be an amino molecule or macromolecule able to act at a reactive site in biospecific chromatography and, for example, constitute a substrate or inhibitor of enzymes, a receptor of hormones, proteins, viruses or bacteria, an antigen or an antibody. Said amino molecule or macromolecule can be particularly a polyamine such as 3-diethylaminopropylamine or N,N-diethylethylenediamine, taurine, ε-amino-caproic acid, lysine, phenylalanine, phenylhydrazine, metaaminophenylboronic acid, bacterial antigens, globulins, particularly gamma globulins, bacterial toxins, viruses or their degradation products such as various viral antigens, cellular receptors such as products of hydrolysis of gangliosides having $NH_2$ functions, in particular the products of hydrolysis of ganglioside $GM_1$ such as lysoglanglioside $G_{M1}$, or the products of partial hydrolysys of ganglioside $G_{M1}$.

It is known that gangliosides have an N-acyl group (acyl derived from a fatty acid such as stearic acid) and at least an N-acetyl group (in position 3 of a galactose fragment), other N-acetyl groups carried by the sialic acid molecules being optionally present. These N-acyl or N-acetyl groups are partially or wholly hydrolizable into —$NH_2$ groups. By analogy with the nomenclature proposed by Suennerholm, Holmgren and Mausson for ganglioside $G_{M1}$, there will be designated below by "lysogangliosides" the products obtained by total hydrolysis of the N-acyl and N-acetyl groups of gangliosides into —$NH_2$ groups. The products of partial hydrolysis of gangliosides, in which certain $NH_2$ groups have been deacylated or deacetylated by alkaline hydrolysis, constitute derivatives that can also be used as amino molecules that can act as reactive sites in the material of the invention. It should be further noted that the materials of the invention on which lysoganglioside $G_{M1}$ is fixed are able to retain the cholera toxin even after treatments in strongly acid media, for example, with a pH1. Now it is known that in an acid medium the gangliosides lose one or more sialic acid molecules and can be transformed into mono-sialo or a-sialo-gangliosides (or -lysogangliosides). Consequently, to fix the cholera toxin, it is possible to use a material according to the invention on which has been fixed, as the amino molecule of formula R'—NH₂, a derivative of any ganglioside (of which the N-acetyl or N-acyl groups have been totally or partially hydrolyzed to make NH₂ groups appear), provided said material is then subjected to acid treatment for a sufficient period to permit transformation of the polysialoganglioside derivatives into mono- or a-sialoganglioside derivatives.

The invention also has for its object a process of preparing new material as defined above.

This process is characterized by the fact that a coating of the porous inorganic support is made by the polysaccharide polymer or by the modified polysaccharide polymer; that, if desired, the polysaccharide coating is transformed into a modified polysaccharide coating; that, if necessary, a cross-linking is performed to stabilize the coating; that said polysaccharide or modified polysaccharide coating is subjected to oxidative scission; that the oxidation product thus obtained is made to react with the amino molecule or macromolecule of formula R'NH₂; and that then the imino derivative obtained is subjected to the action of a reducing agent capable of reducing the imine bond to an amine bond.

The process described above therefore consists particularly in fixing the amino molecule or macromolecule on the polysaccharide or modified polysaccharide coating by the following reactions:

(a) oxidative scission of the alpha-glycol groups to give carbonyl derivatives that can be schematized by the formula R₄—CHO, R₄ being the residue of the polysaccharide molecule after the oxidative scission reaction;

(b) reaction of the amino molecule or macromolecule on the carbonyl groups by the reaction $$R_4\text{---CHO} + R'\text{---NH}_2 \rightarrow R_4\text{---CH}=N\text{---}R' + H_2O;$$

then (c) reduction of the imine bond into a stable amine bond, for example, by nascent hydrogen, according to the reaction $$R_4\text{---CH}=N\text{---}R' + 2H \rightarrow R_3\text{---CH}_2\text{---NH---}R',$$

R₃ being as defined above.

These various chemical transformations can be performed at ambient temperature in a chromatography column.

For the oxidative scission reaction which is known in itself, it is possible to use, for example, lead tetraacetate, periodic acid or one of its derivatives, such as alkaline periodate.

In case the modified polysaccharide polymer is an amino polysaccharide similar to DEAE dextran, it is useful, after the oxidation reaction, to saturate these cation groups with ions, such as halide ions, to avoid any risk of disturbance of the latter reaction of the amino molecule or macromolecule with the aldehyde groups of the support.

For the reduction reaction it is possible to use, for example, a hydride such as sodium borohydride.

To perform the coating of the porous inorganic support by the polysaccharide polymer or by the modified polysaccharide polymer, it is possible to proceed, for example, by introducing the porous inorganic support in powder form into a chromatography column, passing therethrough a buffering solution with a pH of 3 to 12 to equilibrium, introducing a solution of said polymer into the same buffering solution and then eluting until absence of polymer in the eluates is detected, or the porous inorganic support is impregnated with an aqueous solution of said polymer to a pH between 3 and 12, then it is dried in an oven between 50° and 120° C. to a constant weight.

When the amino molecule R'—NH₂, fixed on the porous support by the process just described, is a product of partial or total hydrolysis of a poly- or mono-sialo ganglioside, the process of the invention further includes a final optional stage of acid treatment of the material obtained during a sufficient time to transform hydrolysis product into a corresponding hydrolysis product of a mono- or a-sialo ganglioside. To perform this acid treatment it is possible to use, for example, an aqueous solution of hydrochloric acid with a concentration greater than or equal to 0, 1 N-.

To obtain a cellulose coating it is advantageous to operate as follows: the porous inorganic support is impregnated with a cellulose ester solution, the coated support is dried and subjected to the action of a hydrolysis agent, for example, to the action of an aqueous alkaline solution to hydrolyze the ester groups. In this way, a porous inorganic support, coated with cellulose thus regenerated, is obtained. The cellulose coating thus obtained is very stable and lines the pores of the porous inorganic support perfectly. It is unnecessary to stabilize this coating by cross-linking.

It is possible at this stage to transform the cellulose coating into a modified cellulose coating by making it react with a suitable agent, for example, by making it react with a compound of the formula:

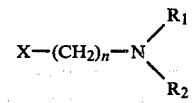

wherein n, R₁ and R₂ are defined as above and X is a halogen atom.

It is possible, for example, to make the poroous inorganic support impregnated with cellulose react with 2-chlorotriethylamine with an alkaline pH and thus obtain a diethylaminoethylcellulose coating.

The invention also has for its object, the process of coating, on a porous inorganic support, cellulose or modified cellulose that has just been described.

The inorganic support that can be used according to the invention should have a well defined controlled porosity. The internal surface of the support should be less than or equal to 100 m²/g and if possible should be between 5 and 80 m²/g. The average pore diameter should be greater than or equal to 25 nm and if possible between 50 and 1000 nm, more exact intervals being advisable depending on the application contemplated. For larger surfaces or slight pore diameters, the internal surface of the support becomes inaccessible to the amino polysaccharide polymer and later to the macromolecules to be separated. According to a preferred embodiment of the invention, the inorganic porous support is silica or alumina and preferably a porous silica support with an anionic character obtained, for example, by the processes described in French Pat. Nos. 1,473,239; 1,473,240; 1,475,929 and 1,482,867. For example, there are used the porous silicas sold by Rhone-Poulenc Chimie Fine under the name SPHEROSILS XOB 030 XOB 015 and XOC 005, these silicas having respective surfaces of 50, 25 and 10 m$^2$/g.

The polysaccharide or modified polysaccharide polymer that can be used to impregnate and cover the internal surface of the inorganic porous support has a molecular weight at least equal to 10$^4$ daltons and preferably between 10$^5$ and 10$^6$ daltons.

The invention also has for its object the use of the novel materials described above in the purification or separation of biological macromolecules.

In a general way, this use consists in employing the affinity properties of the amino molecule or macromolecule grafted on the support, in a chromatography column, either to fixed selectively the biological macromolecules that it is desired to isolate or purify or to retain selectively impurities or other undesired proteins.

This use is characterized by the fact that there is made to pass into a column containing the material, which is the object of this invention, a solution containing the biological macromolecules it is desired to isolate or purify. In case the material fixes biological macromolecules it is desired to purify or isolate, they are then eluted with a suitable solution, making it possible to separate, by known methods, said biological macromolecules from the R'—NH$_2$ molecule to which they are fixed by affinity. For example, in case the biological macromolecules to be isolated are fixed by biospecific affinity on a ligand, the biological macromolecules are separated from their ligand by known separation methods. Of course, depending on the biological macromolecule to be isolated or purified, a porous material will be selected on which is fixed an R'NH$_2$ molecule endowed with affinity for said biological macromolecule.

In case the material fixes impurities, the desired biological macromolecule is collected directly in solution, the porous material then being coated with an R'—NH$_2$ amino molecule endowed with an affinity for the impurity it is desired to eliminate. Then the impurities can be washed out with a suitable solution and the material thus be regenerated for a new operation.

When the biological macromolecule to be isolated or the impurity to be held is fixed on the material of the invention by benefitting from the ion exchange properties of the material, washing out of the molecule thus fixed is done with a solution have suitable pH and molarity.

When it is not desired to use the ion exchange properties of the material of the invention, for example, when it is desired to use only the biospecific affinity properties, it is advisable to use, in the column, solutions of sufficient ionic force to neutralize the ion exchange functions. Thus, in case the material of the invention comprises cationic sites, it is advisable to neutralize the cation groups, for example, by Cl$^\ominus$ ions to eliminate any nonspecific ion type interaction.

In certain cases, it is possible to benefit from both the ion exchange properties and other affinity properties, for example, biospecific affinity properties, of the material of the invention, to separate several different proteins in a single chromatography. For example, with a material having both cation sites and biospecific affinity sites, it is easy to perform the separation of a mixture of three proteins: a first protein with electropositive character, a second protein with electronegative character and a third protein able to be fixed on biospecific affinity sites. Actually, in performing chromatography of such a mixture, the first protein is not fixed and therefore is found at the exit of the column. The second protein is fixed on the cation sites and can be washed out by a solution containing anions able to remove it from the cation sites, for example, a sodium chloride solution. The third protein is fixed on the biospecific sites and be separated from them by a suitable eluent.

Some examples of application according to the invention are given below in a nonlimiting way.

A. PURIFICATION OF CHOLERA TOXIN

It is known that in developing in a suitable culture medium, the vibrio cholerae secretes a toxin called choleragen or enterotoxin which is responsible for the diarrheas caused in men by this germ. After centrifuging and filtering the final culture medium, it is possible to obtain a "crude culture filtrate" containing the cholera toxin mixed with numerous other macromolecules of the initial culture medium or secreted by the vibriones.

The cholera toxin is partially and progressively transformed into a nontoxic form caled choleragenoid. The choleragenoid has a structure close to that of the choleragen, but the choleragen in addition has a polypeptide A chain responsible for the toxicity.

The choleragen and choleragenoid are both fixed selectively on a receptor which was identified in 1973 and which has been called "Ganglioside $G_{M1}$."

Several authors have described the interest of choleragen and choleragenoid for preparing vaccins and it has been thought useful to be able to obtain large amounts of these products.

Purification of choleragen and choleragenoid was described by numerous authors but often requires numerous stages to attain correctly purified and standardized products; and for this reason, these methods are difficult to use industrially. By biospecific affinity chromatography it is theoretically possible to obtain, in a single stage, the desired product in a very purified state. With this in mind, Cuatrecasas (Biochemistry, Vol. 12, No. 21, 1973) described a method for selectively capturing the cholera toxin by affinity chromatography. Agarose chromatographic columns were chemically modified to fix the ganglioside $G_{MI}$ by covalent linking. Thanks to its affinity for $G_{M1}$ fixation of the cholera toxin was actually possible but recovery of this toxin was made difficult because of an extremely strong affinity between the $G_{M1}$ bonded to the agarose and the toxin. This made it necessary to use denaturing media to dissociate the the complex and entailed a denaturing and poor yields at the end of the operation. On the other hand, the method of activiation of agarose that was proposed requires the use of cyanogen bromide which is very dangerous to handle and can therefore involve undesirable complications in a possible industrial development. Further, the derivatives prepared on agarose by the cyanogen bromide method proved to be rather unstable especially for acid pH ($pH<3$); since acidification of the medium was necessary to recover the cholera toxin it can be seen that the life of these supports risked being short in case of industrial utilization.

This application makes it possible to use the effectiveness and rapidity of biospecific affinity chromatographies but by using chromatographic support perfectly suitable for industrial use.

Use of this biospecific affinity support is possible only after having immobilized the selected ligand on the internal face of the pores.

Two different types of ligands, both specific to cholera toxin have been used. The first is a ganglioside $G_{M1}$ derivative endowed with a strong, specific "biochemical affinity" for choleragen or choleragenoid. The second is a cholera antitoxin antibody, endowed with a specific "immunological affinity" for choleragen and choleragenoid. The affinity of the toxin for ganglioside $G_{M1}$ is known to be very strong and probably stronger than the affinity for the antibody. However, after grafting of ganglioside $G_{M1}$ to the surface of the silica by processes that will be indicated, it was found that the resulting affinity between $G_{M1}$ thus grafted and the cholera toxin is entirely reversible. Contrary to the results of Cuatrecasas, it is then possible to recover the cholera toxin under relatively gentle elution conditions. This is not explainable by theory and constitutes a surprising result.

To wash out the cholera toxin fixed on the material of the invention, it is possible to use an acid buffer, for example an acid citrate buffer, a strongly concentrated solution of urea, guanidine, iodide (for example, sodium iodide), thiocyanate (for example, potassium thiocyanate) or any other chaotropic or denaturing agent.

Thanks to this invention, important progress was also made in the stability of the grafted ligands. Actually, it is possible regularly to wash the supports with solutions such as HCl, 0.1 N or NaOH 0.1 N, i.e., from pH 1 to pH 13 without the biospecific affinity qualities suffering from it. Such stabilities do not exist on known supports, for example, with an agarose base which must not be brought to extreme pH.

Finally, on the mechanical plane, the possible yields of 200 to 400 ml/cm$^2$/h and absence of packing of the support have indeed confirmed the interest of these new methods for the contemplated industrial development.

B—OTHER APPLICATIONS

With the material of the invention, made with lysine as the amino molecule, it is possible to benefit from the lysine-plasminogen affinity to isolate and purify the blood plasminogen.

With the material of the invention, made with metaaminophenyl boronic acid as the amino molecule, it is possible reversibly to fix sugars and macromolecules comprising sugars with cis-$\alpha$-glycol function (glycoproteins, nucleic acids and lipopolysaccharides).

In the same way, by using bacterial antigens as the amino molecule, it is possible to fix the correspondings antibodies reversibly; by using gamma globulins as the amino molecule, it is possible to fix the corresponding antigens reversibly; by using bacterial toxins as the amino molecule, it is possible to fix the corresponding antibodies particularly.

The examples illustrate the invention without, however, limiting it.

EXAMPLE 1—GRAFTING OF LYSOGANGLIOSIDE $G_{M1}$ ON POROUS INORGANIC SUPPORT IMPREGNATED WITH SECONDARILY CROSS-LINKED DIETHYLAMINOETHYL DEXTRAN 1.1—The DEAE dextran base support is prepared as follows.

To 10 g of Spherosil XOB 030 are added 30 ml of 7.5% DEAE dextran with pH 11.5. The totality is dried overnight at 80° C., then 30 ml of a 1.5% solution of butanedioldiglycidylether in ethyl ether are added. The ether is evaporated under an air current, then the totality is allowed to stand 15 hours at 80° C. to obtain the cross-linking of the DEAE dextran.

1.2—The ganglioside solution is prepared by ion exchange chromatography on porous silica impregnated with DEAE dextran by the method described in example 8 of French patent application No. 76 23176.

The crude ganglioside solution thus obtained contains about 40% ganglioside $G_{m1}$ useful in the present application.

The two N-acetyl functions and the N-acyl function of ganglioside $G_{m1}$ are then hydrolyzed into $NH_2$ amino functions by alkaline hydrolysis by the process previously described by Holmgren, Mansson and Svennerholm, Medical Biology (1974), 52 229–233. The product thus obtained is called lysoganglioside, it has three $NH_2$ functions per molecule. After freeze-drying, the resulting powder is dissolved in an 0.01 M carbonate buffer with pH 9 containing 20 g/l NaCl in a concentration of 1 mg/ml. One (1) ml of this solution contains about 370 $\mu$g sialic acid per ml.

1.3—Periodic oxidation of the support

To 10 g of Spherosil XOB 030, impregnated with secondarily cross-linked DEAE dextran, are added 100 ml of an 0.02 M aqueous solution of sodium periodate (pH close to 4.5). The oxidation time is 2 h, ambient temperature is well suited for this operation.

The support is then washed in an 0.01 M solution of sodium carbonate, with pH 9, to which have been added 20 g/l of sodium chloride. The high ionic force of this buffer is intended to saturate the cation groups of the DEAE dextran that has been cross-linked and oxidized, with $Cl^{\ominus}$ ions and to prevent them from further fixing the lysoganglioside by electrostatic forces that are in danger of damaging the reaction of the amino groups on the aldehyde functions of the support.

At this stage it is easy to show the aldehyde functions of the oxidized support. In the presence of Schiff reagent, a deep violet pink coloring appears.

1.4—Grafting of the lysoganglioside

The above support is washed then 50 ml of lysoganglioside $G_{m1}$ solution are added. After a 2-hour contact period, the contact supernatant is decanted. With a dosage of sialic acid it is easy to show that almost all (95–11%) of the lysoganglioside has been coupled.

The support is rinsed in carbonate buffer pH 9. At this stage it is easy to show also that the coloring of the support with Schiff reagent is much weaker than in the preceding stage, indicating a good fixation of the lysoganglioside on the aldehyde functions of the oxidized support.

1.5—Reduction by sodium borohydride

To the preceding support are added 50 ml of an 0.2 M solution of $NaBH_4$ in water (pH 9). After a 2-hour contact period at ambient temperature, the support is rinsed in water then put in the column.

After balancing in the selected chromatography buffer (0.01 M phosphate buffer of pH 7.2 containing 20 g/l of NaCl), the biospecific affinity column is ready to use.

At this stage no trace of the aldehyde function is any longer detectable with the Schiff reagent. The aldehyde functions not having reacted with the lysoganglioside have themselves been transformed into primary alcohol functions.

It should be noted that the support thus obtained can function perfectly as an ion exchanger. If it is desired to eliminate the ionic interactions with the proteins to retain only the biospecific interactions, it is therefore important to have a minimal ionic force. In practice, a minimal concentration of 10 g/l NaCl suffices to eliminate the ion exchange effect.

1.6—By rigorously following the same technique it was possible also effectively to graft lysine, phenylalanine, phenylhydrazine, metaaminophenylboronic acid. It is thought that it is possible also to graft any molecule carrying $NH_2$ functions such as for example: an enzyme inhibitor or substrate, a receptor of hormones, proteins, viruses or bacteria, an antigen or an antibody, and to use each of these supports in biospecific affinity chromatography.

EXAMPLE 2—GRAFTING OF LYSOGANGLIOSIDE $G_{M1}$ ON POROUS INORGANIC SUPPORT IMPREGNATED WITH CELLULOSE 2.1—Impregnation in cellulose To 10 g of Spherosil XOC 005 (or any other porous inorganic support) are added 30 ml of a 3% cellulose acetate acetonic solution (cellulose propionate or other esters that are soluble in an organic medium and hydrolyzable can also be suitable provided they can restore the original cellulose by alkaline hydrolysis).

The totality is dried in a hot air current. The powder can then be sifted, if necessary, and mounted in the column.

A washing with 10 l of an 0.1 N NaOH aqueous solution is then performed continuously with a delivery of 500 ml/h for an entire night. After this alkaline hydrolysis, the column can be washed with acetone or water regardless of the pH, the cellulose thus regenerated is no longer soluble and remains perfectly on the inside of the pores of the porous inorganic support, which it lines all the better because the initial polymer has been able easily to reach the totality of the internal surface. Use of cellulose esters with as low a molecular weight as possible is advised for this reason.

2.2—Preparation of the lysoganglioside $G_{M1}$ solution with amino functions.

Same conditions as in paragraph 1.2.

2.3—Periodic oxidation of the support

Same conditions as in paragraph 1.3.

2.4—Grafting of the lysoganglioside

Same conditions as in paragraph 1.4.

2.5—Reduction by sodium borohydride $NaBH_4$

Same conditions as in paragraph 1.5.

Unlike the support prepared according to the preceding example, the present one does not have ion exchange properties, and therefore can be used, optionally, for lower ionic forces, in case this could be an advantage. For the affinity between lysoganglioside and cholera toxin this makes no difference.

2.6—By rigorously following the same technique it was possible to graft anion exchange functions particularly with 3-diethylaminopropylamine or N,N-diethylethylenediamine and use the supports thus obtained in protein chromatography.

2.7—And still following the same technique it was possible to graft various ligands with amino functions including lysine, phenylalanine, phenylhydrazine, metaaminophenylboronic acid and use the supports thus obtained in biospecific affinity chromatography.

In the same way it is possible to graft any molecule with amino function(s) such as, for example: an enzyme substrate or inhibitor, a receptor of hormones, proteins, viruses or bacteria, an antigen or antibody and use each of these supports in biospecific affinity chromatography.

EXAMPLE 3—APPLICATION TO ISOLATION AND PURIFICATION OF CHOLERA TOXIN

The columns described in the preceding examples (except 2.6) can be used in biospecific chromatography. The presence of 10 to 20 g/l of NaCl in the chromatography buffer is recommended to eliminate any ion type nonspecific interaction with the electric charges of the ion exchange functions, the ligands or proteins present on the support.

By passing a filtrate of vibro cholerae culture, to which have been added 10 g/l of NaCl, on each of these columns, it is easy to verify that the choleragen and choleragenoid are caught on the support. Actually, provided the maximal fixation capacity of the column is not exceeded, the filtrate obtained at the column output is completely free of toxic activity measurable by known tests.

After washing with the chromatography buffer to eliminate unfixed proteins, it is possible to recover the fixed choleragen or choleragenoid by elution with 0.05 M citrate-citric acid buffer pH 2.8. The resulting denaturing is apparently negligible since the resulting yields vary from 50 to 100%, measured by standard determination tests of cholera toxin.

The purity of the preparation can be evaluated by chromatography on Sephadex G-200 (choleragen gives a peak corresponding to a molecular weight of 84,000, choleragenoid gives a peak corresponding to a molecular weight of 56,000) or by immunochemical methods with control antisera. (A culture antifiltrate antiserum not having cholera antitoxin antibodies should not give a precipitation line with these purified preparations.)

A 10-gram column made according to one of the methods described in the above examples makes it possible to treat amounts of culture filtrate from 500 ml to 10 l, the exact amount depending obviously on several parameters, namely the amount of toxin present in the culture filtrate and the amount of $G_{m1}$ in the raw ganglioside solution.

The following are possible applications;

preparing a solution of purified choleragen and choleragenoid that can be used to prepare a vaccine, ridding a culture filtrate of vibrones cholerae of any trace of choleragen and choleragenoid, and preparing antisera in regard to these two types of solutions.

EXAMPLE 4—SEPARATION OF THE CONSTITUENTS OF A MIXTURE OF GAMMA GLOBULIN, ALBUMIN AND CHOLERA TOXINS IN A SINGLE CHROMATOGRAPHY

This example is intended to demonstrate the possibilities of using the material described in example 1 simultaneously in ion exchange chromatography and affinity chromatography. Contrary to what was done in example 3, sodium chloride is not added to the chromatography solvent which contains an artifial mixture of three proteins: gamma globulins, albumin and cholera toxin. The gamma globulins which exhibit an electropositive character are not adsorbed on the modified DEAE dextran layer, while the albumin which exhibits an electronegative character is fixed on this layer. The cholera toxin is fixed on the lysoganglioside $G_{M1}$ sites. By using a chromatography buffer of slight ionic force (0.01 M phosphate buffer, pH 6.8) gamma globulins are found at the column output in the form of an unadsorbed peak. By subsequent elution with a buffer containing 10 g per liter of sodium chloride, the albumin is displaced and washed out. Later elution with a citrate buffer of pH 2.8 makes it possible then to wash out the cholera toxin.

We claim:

1. A process for the preparation of a porous solid material for use in a chromatography column and capable of fixing reversibly biological macromolecules comprising:

(1) coating a porous inorganic support with a polysaccharide polymer having $\alpha$-glycol groups which undergo oxidative scission, said polysaccharide polymer being selected from the group consisting of polysaccharide polymer, per se and a modified polysaccharide polymer of the formula 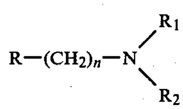 wherein R represents the polysaccharide polymer residue, n is a whole number ranging from 1 to 10 and $R_1$ and $R_2$ each independently represent lower alkyl or hydroxy lower alkyl;

(2) subjecting said polysaccharide polymer to an oxidative scission reaction to produce a polymer having the formula $R_4$—CHO wherein $R_4$ is the residue of the resulting oxidized polysaccharide polymer;

(3) reacting said resulting polymer with an amino molecule or macromolecule having the formula $R'$—$NH_2$ wherein R' is the residue of said amino molecule or macromolecule, to produce a polysaccharide polymer having the formula $R_4$—CH=N—R' wherein $R_4$ and R' have the meanings given above.

(4) and reducing the imine bond in the polysaccharide polymer resulting from step (3) to a stable amine bond.

2. The process of claim 1 wherein the oxidative scission reaction is performed with a member selected from the group consisting of periodic acid and alkaline periodate.

3. The process of claim 1 wherein the reduction of the imine bond to a stable amine bond is carried out with sodium borohydride.

4. The process of claim 1 wherein the porous inorganic support is a metal oxide selected from the group consisting of silica, alumina, magnesia, a titanium oxide, a glass, a silicate, a borosilicate and kaolin.

5. The process of claim 4 wherein the porous inorganic support has an internal surface less than or equal to 100 $m^2/g$.

6. The process of claim 4 wherein the porous inorganic support has an internal surface between 5 and 80 $m^2/g$.

7. The process of claim 4 wherein the porous inorganic support has an average pore diameter of at least 25 nm.

8. The process of claim 4 wherein the porous inorganic support has an average pore diameter of between 50 and 1000 nm.

9. The process of claim 1 wherein said polysaccharide polymer is selected from the group consisting of dextran, cellulose, starch, diethylaminoethyl dextran, diethylaminoethyl starch and diethylaminoethyl cellulose.

10. The process of claim 1 wherein said polysaccharide polymer is a crosslinked polysaccharide polymer.

11. The process of claim 10 wherein said polysaccharide polymer is crosslinked with a crosslinking agent selected from the group consisting of 1,4-butanedioldiglycidylether, eipchlorohydrin, eipbromohydrin and an epoxide of the of the formula 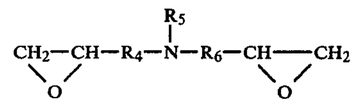 wherein $R_5$ is alkyl having 1-20 carbon atoms and $R_4$ and $R_6$ each represent a hydrocarbon chain having 1-10 carbon atoms.

12. The process of claim 1 wherein said polysaccharide polymer is cellulose.

13. The process of claim 1 wherein said amino molecule or macromolecule is selected from the group consisting of 3-diethylaminopropyl amine, N,N-diethylethylenediamine, lysine, phenylalanine, phenylhydrazin, taurine, $\epsilon$-aminocaproic acid, meta-aminophenylboronic acid, bacterial antigen, a globulin, a bacterial toxin, a virus and a cell receptor.

14. The process of claim 13 wherein said cell receptor is a product resulting from the total or partial hydrolysis of the N-acyl or N-acetyl groups of a ganglioside.

15. The process of claim 14 wherein said cell receptor is lysoganglioside $G_{M1}$.

16. A porous solid material prepared by the process of claim 1.

17. The porous solid material of claim 16 wherein the porous inorganic support is silica, the polysaccharide polymer is diethylaminoethyl dextran crosslinked with butanedioldiglycidylether, and the amino molecule or macromolecule is lysoganglioside.

18. The porous solid material of claim 16 wherein the porous inorganic support is silica, the polysaccharide polymer is diethylaminoethyl dextran crosslinked with butanedioldiglycidylether and the amino molecule or macromolecule is lysine, phenylalanine, phenylhydrazine or metaaminophenylboronic acid.

19. The porous solid material of claim 16 wherein the porous inorganic support is silica, the polysaccharide polymer is cellulose and the amino molecule or macromolecule is lysoganglioside.

20. The porous solid material of claim 16 wherein the porous inorganic support is silica, the polysaccharide polymer is cellulose and the amino molecule or macromolecule is 3-diethylaminopropylamine or N,N-diethylethylenediamine.

21. The porous solid material of claim 16 wherein the porous inorganic support is silica, the polysaccharide polymer is cellulose and the amino molecule or macromolecule is lysine, phenylalanine, phenylhydrazine or metaaminophenylboronic acid.

* * * * *

UNITED STATES PATENT AND TRADEMARK OFFICE
CERTIFICATE OF CORRECTION

PATENT NO. : 4,308,254
DATED : December 29, 1981
INVENTOR(S) : Jean-Louis Tayot and Michel Tardy It is certified that error appears in the above—identified patent and that said Letters Patent is hereby corrected as shown below:

On the title page, under Foreign Application Priority Data: "Sep. 19, 1981" should read -- Sep. 19, 1977 --.

Signed and Sealed this

Eighth Day of June 1982

[SEAL]

Attest:

GERALD J. MOSSINGHOFF

*Attesting Officer*  *Commissioner of Patents and Trademarks*